United States Patent
Lewis et al.

(10) Patent No.: US 11,144,944 B1
(45) Date of Patent: Oct. 12, 2021

(54) SYSTEM FOR DETERMINING A SUBSTITUTE GROCERY ITEM BASED UPON A DETERMINED MEDICATION INTERACTION AND RELATED METHODS

(71) Applicant: Inmar Clearing, Inc., Winston-Salem, NC (US)

(72) Inventors: Courtney M. Lewis, Wintson-Salem, NC (US); Jeff Clouse, Jamestown, NC (US); Diana Medina, Winston-Salem, NC (US); Teva Moore, Winston-Salem, NC (US); Alise Raak, Winston-Salem, NC (US); Rob Small, Winston-Salem, NC (US); Chris Smith, Advance, NC (US)

(73) Assignee: INMAR CLEARING, INC., Winston-Salem, NC (US)

( * ) Notice: Subject to any disclaimer, the term of this patent is extended or adjusted under 35 U.S.C. 154(b) by 0 days.

(21) Appl. No.: 16/428,255

(22) Filed: May 31, 2019

(51) Int. Cl.
| | |
|---|---|
| *G06Q 30/02* | (2012.01) |
| *G16H 50/30* | (2018.01) |
| *G06Q 30/06* | (2012.01) |
| *G06K 19/06* | (2006.01) |

(52) U.S. Cl.
CPC ... *G06Q 30/0222* (2013.01); *G06K 19/06037* (2013.01); *G06Q 30/0631* (2013.01); *G16H 50/30* (2018.01)

(58) Field of Classification Search
CPC .. G06Q 30/02; G06Q 30/016; G06Q 30/0254; G06Q 30/0222; G06Q 30/0631; H04L 67/306; H04W 4/14; G16H 50/30; G06K 19/06037
See application file for complete search history.

(56) References Cited

U.S. PATENT DOCUMENTS

| | | | | |
|---|---|---|---|---|
| 7,945,473 | B2 * | 5/2011 | Fano | G06Q 30/0269 |
| | | | | 705/14.1 |
| 9,092,783 | B2 * | 7/2015 | Guday | G06Q 30/0211 |
| 9,292,565 | B2 | 3/2016 | Bhagwan et al. | |
| 2008/0052169 | A1 * | 2/2008 | O'Shea | G06Q 30/02 |
| | | | | 705/14.17 |
| 2011/0015984 | A1 * | 1/2011 | Galinos | G06Q 30/0225 |
| | | | | 705/14.26 |
| 2011/0166881 | A1 * | 7/2011 | Brazzo | G06Q 30/02 |
| | | | | 705/3 |
| 2011/0307318 | A1 * | 12/2011 | LaPorte | G06Q 30/0207 |
| | | | | 705/14.33 |
| 2012/0041815 | A1 * | 2/2012 | Gangi | G06Q 20/40 |
| | | | | 705/14.38 |

(Continued)

*Primary Examiner* — Thuy N Nguyen
(74) *Attorney, Agent, or Firm* — Allen, Dyer, Doppelt + Gilchrist, P.A.

(57) ABSTRACT

A system may include a remote device and a server. The server may be configured to store a grocery items purchase history for a given user, and determine a medication to be dispensed to the given user. The server may also be configured to compare the medication to the grocery items purchase history and determine a grocery item having an interaction with the medication, and determine a substitute grocery item for the grocery item having the interaction with the medication. The server may generate a digital promotion for the substitute grocery item, and communicate the digital promotion to the remote device.

10 Claims, 4 Drawing Sheets

(56) References Cited

U.S. PATENT DOCUMENTS

| | | | |
|---|---|---|---|
| 2012/0160911 A1* | 6/2012 | Smith | G06Q 20/32 235/379 |
| 2012/0209749 A1* | 8/2012 | Hammad | G06Q 20/204 705/27.1 |
| 2012/0323664 A1* | 12/2012 | Klems | G06Q 30/02 705/14.26 |
| 2013/0024211 A1* | 1/2013 | Monteforte | G06Q 30/00 705/3 |
| 2013/0110607 A1* | 5/2013 | Basmajian | G06Q 30/0238 705/14.26 |
| 2013/0173372 A1* | 7/2013 | Misra | G06K 7/1408 705/14.23 |
| 2013/0179250 A1* | 7/2013 | Nguyen | G06Q 30/0238 705/14.36 |
| 2013/0191213 A1* | 7/2013 | Beck | G06Q 20/3224 705/14.53 |
| 2013/0196297 A1* | 8/2013 | Anwar | G16H 40/67 434/236 |
| 2013/0211890 A1* | 8/2013 | Heitmueller | G06Q 20/387 705/14.13 |
| 2014/0278878 A1* | 9/2014 | Wiegand | G06Q 30/0233 705/14.25 |
| 2015/0046240 A1* | 2/2015 | Moreton | G06Q 30/0225 705/14.17 |
| 2015/0100398 A1* | 4/2015 | Narayanaswami | G06Q 30/0207 705/14.16 |
| 2015/0332374 A1* | 11/2015 | Fano | G06Q 30/0631 705/14.66 |
| 2016/0012194 A1* | 1/2016 | Prakash | G16H 40/40 705/2 |
| 2016/0132921 A1* | 5/2016 | Calvo Martinez | G06Q 30/0239 705/14.36 |
| 2018/0139067 A1* | 5/2018 | Josyula | H04M 3/42178 |
| 2019/0018932 A1* | 1/2019 | Groarke | G06Q 20/145 |
| 2020/0098466 A1* | 3/2020 | Murdoch | H04W 4/021 |

* cited by examiner

US 11,144,944 B1

SYSTEM FOR DETERMINING A SUBSTITUTE GROCERY ITEM BASED UPON A DETERMINED MEDICATION INTERACTION AND RELATED METHODS

TECHNICAL FIELD

The present invention relates to the field of medications, and more particularly, to medication interactions and related methods.

BACKGROUND

A loyalty program is one type of marketing strategy to encourage customers to continue to shop at a given retail establishment. A loyalty program may track purchases made by a customer and reward the customer with one or more promotions or discounts, for example, based upon quantities and types of items purchased.

A medication interaction is an unintentional effect of using a medication. A medication interaction typically occurs when two or more medications interact to have the unintentional effect. A medication interaction may also occur between a medication and a food or beverage. As the number of medications a given user is taking increases, so too does the risk of a medication interaction.

U.S. Patent Application Publication No. 2011/0166881 to Brazzo et al. is directed to a system for generating food recommendations. More particularly, Brazzo et al. discloses making food recommendations using a pharmacy management system. A given patient's current medical condition(s), or disease state profile, is inferred from a listing of currently prescribed medications in the patient's drug profile. International Classification of Disease (ICD) codes, or other unique identifiers, are linked to specific drug codes, such as National Drug Code (NDC) numbers, to generate a tentative medical condition(s), or disease state profile for the patient. The ICD codes, or other unique identifiers, interface with a nutritional database to generate food recommendations. The system may eliminate foods from the recommendation that may be contraindicated in any particular disease state, interact with any medication currently prescribed, or which constitute a food to which the patient may be allergic. Savings coupons may be printed for the food recommendations. The coupons and recommendations may be communicated to the user via a user interface (e.g., where the user logs in).

SUMMARY

A system may include a remote device and a server. The server may be configured to store a grocery items purchase history for a given user, and determine a medication to be dispensed to the given user. The server may also be configured to compare the medication to the grocery items purchase history and determine a grocery item having an interaction with the medication, and determine a substitute grocery item for the grocery item having the interaction with the medication. The server may generate a digital promotion for the substitute grocery item, and communicate the digital promotion to the remote device.

The server may be configured to generate a notification based upon the determined grocery item having an interaction with the medication and communicate the notification to the remote device. The server may be configured to determine the substitute grocery item based upon a medical condition associated with the medication, for example.

The remote device may include a mobile wireless communications device associated with the given user. The remote device may include a pharmacy point-of-sale (POS) terminal, for example.

The pharmacy POS terminal may be configured to print a grocery list including the substitute item, for example. The pharmacy POS terminal may be configured to print the digital promotion in the form of a machine recognizable code.

The system may further include a mobile wireless communications device associated with the given user and configured to obtain the digital promotion based upon the machine recognizable code, for example. The machine recognizable code may include a quick response (QR) code.

A method aspect is directed to a method of communicating a digital promotion. The method may include using a server to store a grocery items purchase history for a given user, and determine a medication to be dispensed to the given user. The method may also include using the server to compare the medication to the grocery items purchase history and determine a grocery item having an interaction with the medication, and determine a substitute grocery item for the grocery item having the interaction with the medication. The method may further include using the server to generate the digital promotion for the substitute grocery item, and communicate the digital promotion to a remote device.

A computer readable medium aspect is directed to a non-transitory computer readable medium for communicating a digital promotion. The non-transitory computer readable medium includes computer executable instructions that when executed by a processor cause the processor to perform operations. The operations may include storing a grocery items purchase history for a given user and determining a medication to be dispensed to the given user. The operations may also include comparing the medication to the grocery items purchase history and determine a grocery item having an interaction with the medication and determining a substitute grocery item for the grocery item having the interaction with the medication. The operations may further include generating the digital promotion for the substitute grocery item, and communicating the digital promotion to a remote device.

DETAILED DESCRIPTION

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout, and prime notation is used to indicate similar elements in alternative embodiments.

Figure 1:
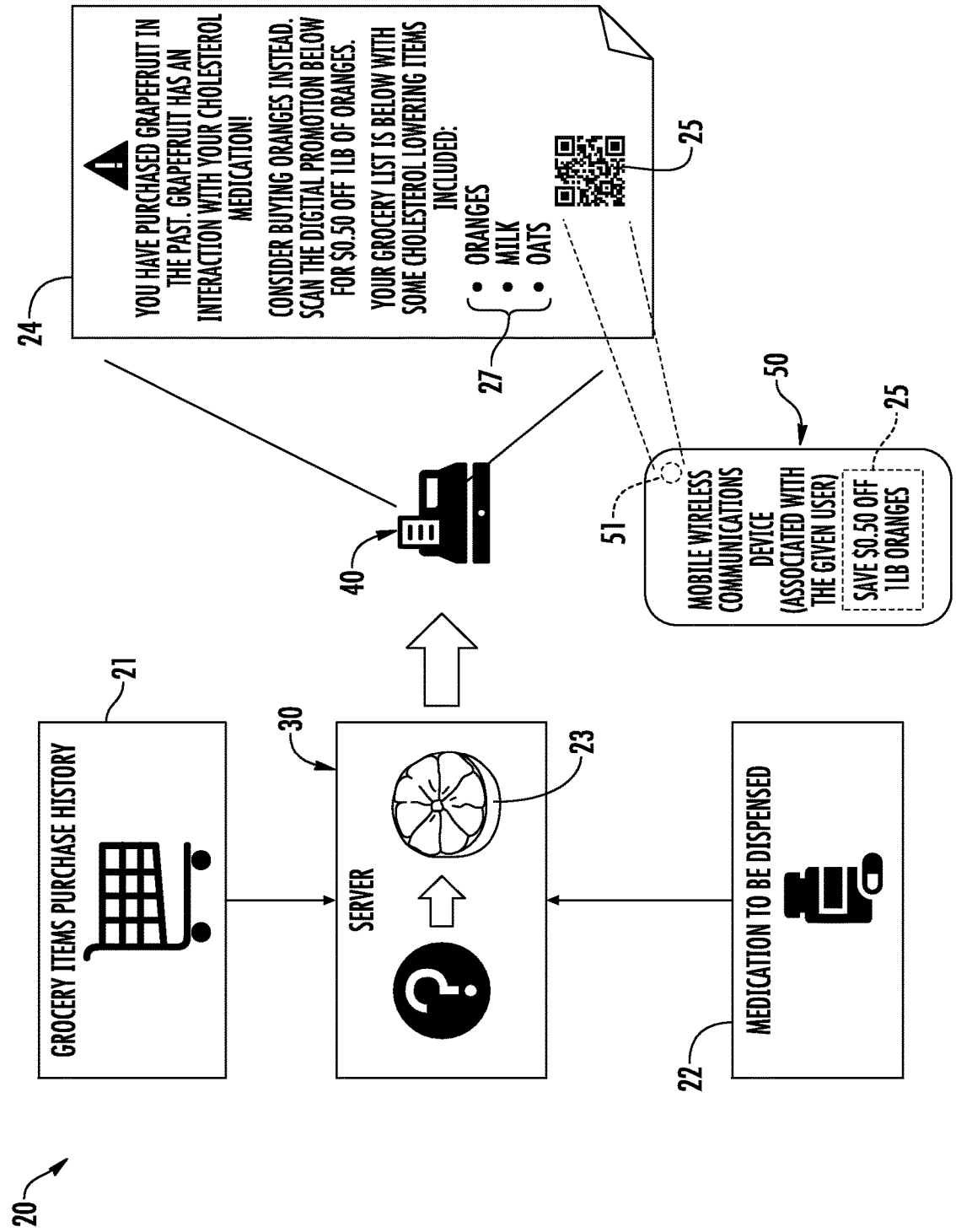
FIG. 1 is a schematic diagram of a system in accordance with an embodiment.
Figure 2:
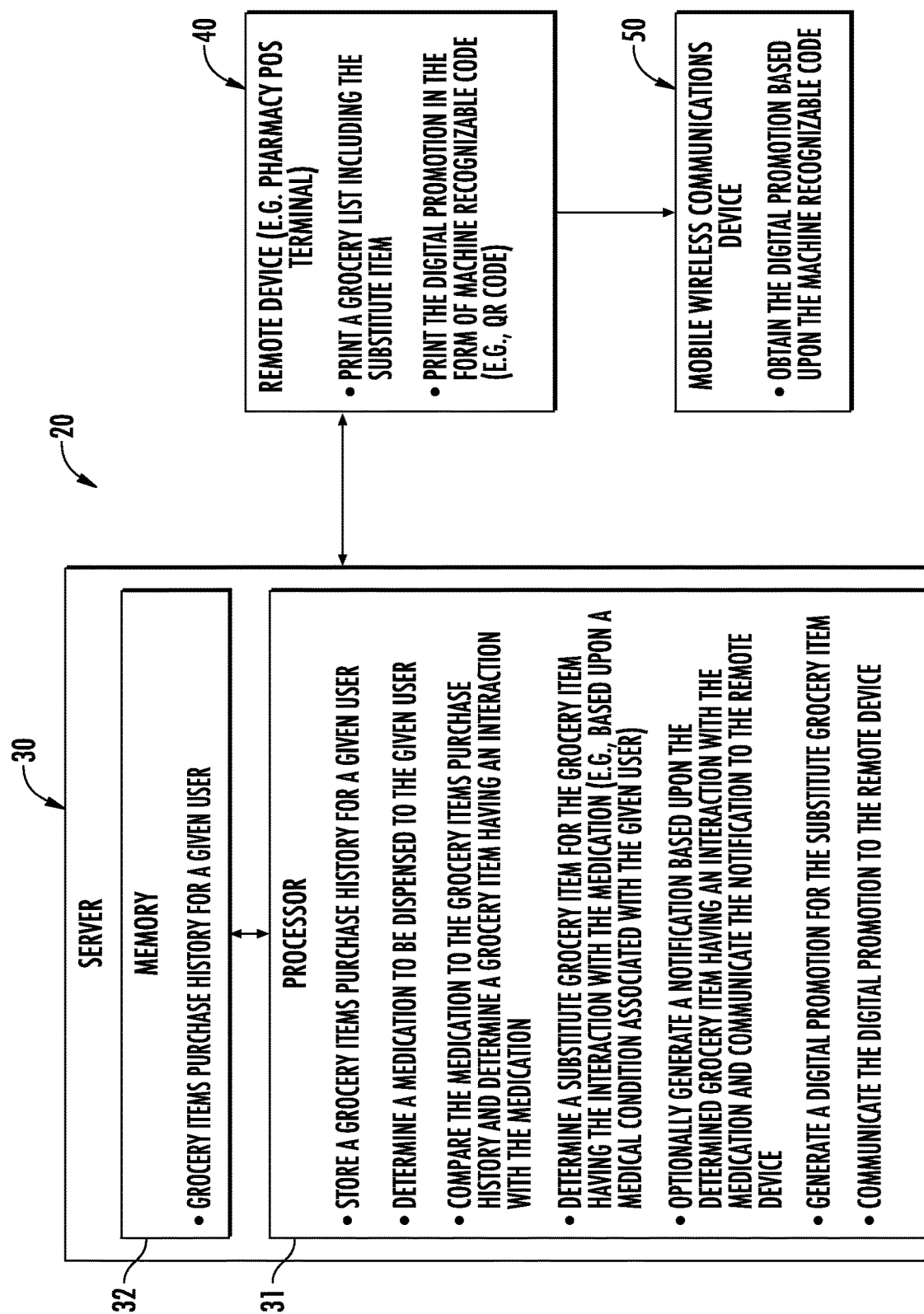
FIG. 2 is a schematic block diagram of the system of FIG. 1.

Referring initially to FIGS. 1 and 2, a system 20 includes a remote device 40 and a server 30. The server 30 includes a processor 31 and an associated memory 32. While operations of the server 30 will be described herein with respect to the server, those skilled in the art will appreciate that the operations of the server are performed by cooperation between the processor 31 and the memory 32.

Figure 3:
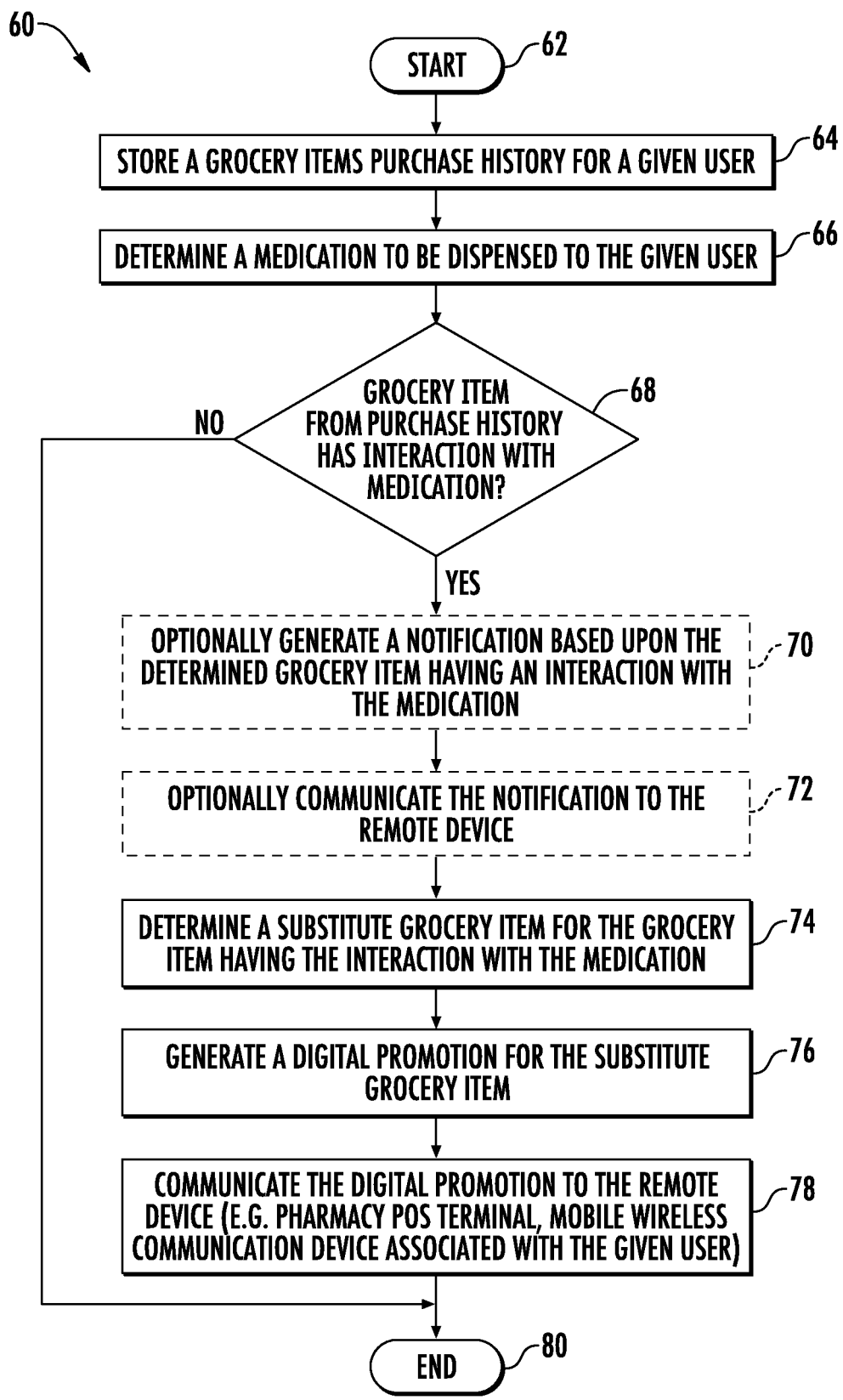
FIG. 3 is a flow diagram illustrating operation of the server of the system of FIG. 1.

Referring now additionally to the flowchart 60 in FIG. 3, beginning at Block 62, operations of the server 30 will now be described. The server 30 stores a grocery items purchase history 21 for a given user, for example, in the memory 32 (Block 64). For example, the server 30 may be configured to operate a loyalty program for a retail or grocery store. Accordingly, the server 30 may store items, such as, for example, groceries, pharmaceuticals, and/or other retail products purchased by the given user at the retail store. Each of the items in the grocery items purchase history 21 may have a unique product identifier associated therewith, for example, a uniform product code (UPC). The unique product identifier along with a user identifier (e.g., loyalty ID, phone number, email address, etc.) may be stored in the memory 32. Items being purchased may be added to the grocery items purchase history 21, for example, in real-time as items are being scanned at a point-of-sale (POS) terminal at the retail store.

At Block 66, the server 30 determines a medication to be dispensed to the given user. More particularly, the server 30 may determine that the given user has submitted a prescription to be filled at a pharmacy associated with a grocery store (e.g., the in-house pharmacy at the grocery store). The server 30 may identify or determine the medication to be dispensed based upon matching the given user's name, which is typically associated with the prescription, to a name associated with the loyalty program, to a loyalty program identifier, or to another identifier such that the server can associate the medication to be dispensed to the grocery items purchase history 21. As will be appreciated by those skilled in the art, the grocery store and pharmacy within the grocery store often operate mutually exclusive systems. That is, for example, a given user's medication information and the given user's grocery items purchase history 21 are maintained in separate mutually exclusive systems.

At Block 68, the server 30 determines whether a grocery item from the grocery items purchase history has an interaction with the medication 22. The server 30 determines whether a medication from the grocery items purchase history 21 has an interaction with the medication by comparing the medication 22 to the grocery items purchase history 21. For example, the server 30 may store a lookup table in the memory 32 that includes a name, identifier, and/or elements or ingredients of the medication and an associated list of one or more grocery items (e.g., based upon a unique identifier associated with the grocery items) that have an interaction with the medication 22. The interaction may be determined based upon an ingredient of the grocery items of the grocery items purchase history 21.

If at Block 68 there is no determined interaction with the medication, operations end at Block 80. If at Block 68, a grocery item is determined to have an interaction with the medication, the server 30 generates a notification 24 that identifies the interaction with the medication (Block 70) and communicates the notification 24 to the remote device 40 (Block 72). The remote device 40 may be in the form of a POS terminal, for example, located at a pharmacy desk of the grocery store. The notification 24 may be printed at the POS terminal 40 and handed to the given user by a pharmacist or pharmacy technician, for example. In some embodiments, the server 30 may not generate and communicate a notification 24. Moreover, the server 30 may additionally communicate the notification 24 to a mobile wireless communications 50 device associated with the given user.

At Block 74, the server 30 determines a substitute grocery item 23 for the grocery item having the interaction with the medication. The substitute grocery item 23 may be any food or grocery item that does not have an interaction with the medication 22.

The server 30 may determine the substitute grocery item 23, for example, based upon a medical condition associated with the medication. More particularly, the server 30 may determine, based upon the medication itself and/or an ingredient thereof, a medical condition (e.g., via a lookup table), and determine the substitute grocery item 23 based upon the medical condition. In other words, the server 30 may determine the substitute grocery item 23 to address, counter, or aid in treatment of the medical condition. For example, the server 30 may store, in the lookup table, foods or grocery items that are complementary to the medical condition (e.g., for diabetes, low sugar grocery items).

The server 30 generates a digital promotion 25 for the substitute grocery item 23 at Block 76 and communicates the digital promotion to the remote device 40 or pharmacy POS terminal at Block 78. The digital promotion 25 has a promotional value associated therewith that is applied toward the purchase of the substitute grocery item 23. The promotional value may be for a portion of the purchase price of the substitute grocery item 23 or a full purchase price of the substitute grocery item. The digital promotion 25 may be redeemable at the grocery store POS terminal and/or the pharmacy POS terminal 40.

The pharmacy POS terminal 40 may print the digital promotion 25, for example, along with the notification 24 described above. The digital promotion 25 may be printed in a machine recognizable code, for example, a quick response (QR) code. Of course, the digital promotion 25 may be printed in other machine recognizable formats.

The pharmacy POS terminal 40 may print the digital promotion without the notification in some embodiments, for example, where the notification was communicated to the mobile wireless communications device 50 associated with the given user. The server 30 may also communicate the digital promotion 25 to the user's mobile wireless communications device 50, for example, for storage in a digital wallet. Of course, the server 30 may print the notification 24 and digital promotion 25 even if the notification and digital promotion were communicated to the user's mobile wireless communications device 50. The printout from the pharmacy POS terminal 40 may be handed to the given user when he or she visits the pharmacy for dispensing of their medication.

The pharmacy POS terminal 40 may also, in some embodiments, print a grocery list 27 that includes the substitute grocery item 23. The grocery list 27 may include additional grocery items that may be considered substitute items, for example, relatively healthy food options that may helpful for addressing the medical condition. The grocery list 27 may also be imported from upon the given user's online or in-app grocery list based upon the user's name, loyalty identifier, or other identifying source.

Additionally, in some embodiments, for example, where the server 50 does not communicate the digital promotion 25 to the user's mobile wireless communications device, the user, by way of a camera 51 of the mobile wireless communications device may obtain the digital promotion based upon the machine recognizable code. Upon obtaining the digital promotion 25, the user's mobile wireless communications device 50 may store the digital promotion in a digital wallet for redemption. Operations end at Block 80.

In one example implementation of the system 20, a given user may be filling a prescription (initial or refill) of a cholesterol lowering medication that includes statins. The given user may also be an avid purchaser of grapefruits and/or grapefruit juice. Grapefruit juice and grapefruits have been documented to have a blocking effect of the enzymes that breakdown or metabolize the statins. Accordingly, too much of the statin may remain in the body. However, grapefruits and grapefruit juice are typically considered to be a good source of vitamin C and potassium. Accordingly, the system 20 described herein may advantageously generate a notification 24 of the grapefruit/statin interaction and determine a substitute product 23 that is also a good source of vitamin C and potassium and lowers cholesterol, for example, other citrus or fruit. The system 20 also generates and communicates a digital promotion 25 to the given user for the substitute product, for example, to entice the given user to purchase the substitute product.

By using the grocery items purchase history 21 as a basis for determining whether a grocery item is determined to have an interaction, the server 30 is able to determine whether the given user has an affinity for the given grocery item or ingredient having the interaction (e.g., the given user regularly purchases the grocery item) prior to dispensing of the medication. This may advantageously alert the given user and/or a pharmacist/pharmacy technician of a specific grocery item rather than provide an extensive listing of grocery items having an interaction.

The server 30 may also determine from the grocery items purchase history 21 whether a grocery item is a "single-time" or rare purchase for the given user. Accordingly, the server 30 may, in some embodiments, determine that a grocery item has a medication interaction based upon exceeding a score. For example, the server 30 may determine how much of a given grocery item the user typically purchases and determines whether that amount of the grocery item exceeds a threshold score to be determined as having an interaction. The server 30 may determine or generate the score by assigning relative weights to certain interactions.

For example, if a particular interaction is minimal, and the given user consumes relatively small amounts of the grocery item capable of causing the interaction based upon the grocery items purchase history 21, the server 30 may determine a relatively low score, and thus not determine (for purposes of generating a notification and/or generating a digital promotion) that the grocery item has an interaction. If, for example, the level of interaction is relatively high, regardless of the amount of the grocery item, a relatively high score may be assigned, and thus the server 30 determines that an interaction with the grocery item exists. In other words, the determination of whether an interaction exists may be based upon the score. Moreover, in some embodiments, the promotional value of the digital promotion 25 may be based upon the score. For example, if the score is relatively high, the digital promotion 25 may have a higher promotional value to entice the given user the purchase the substitute grocery item.

Figure 4:
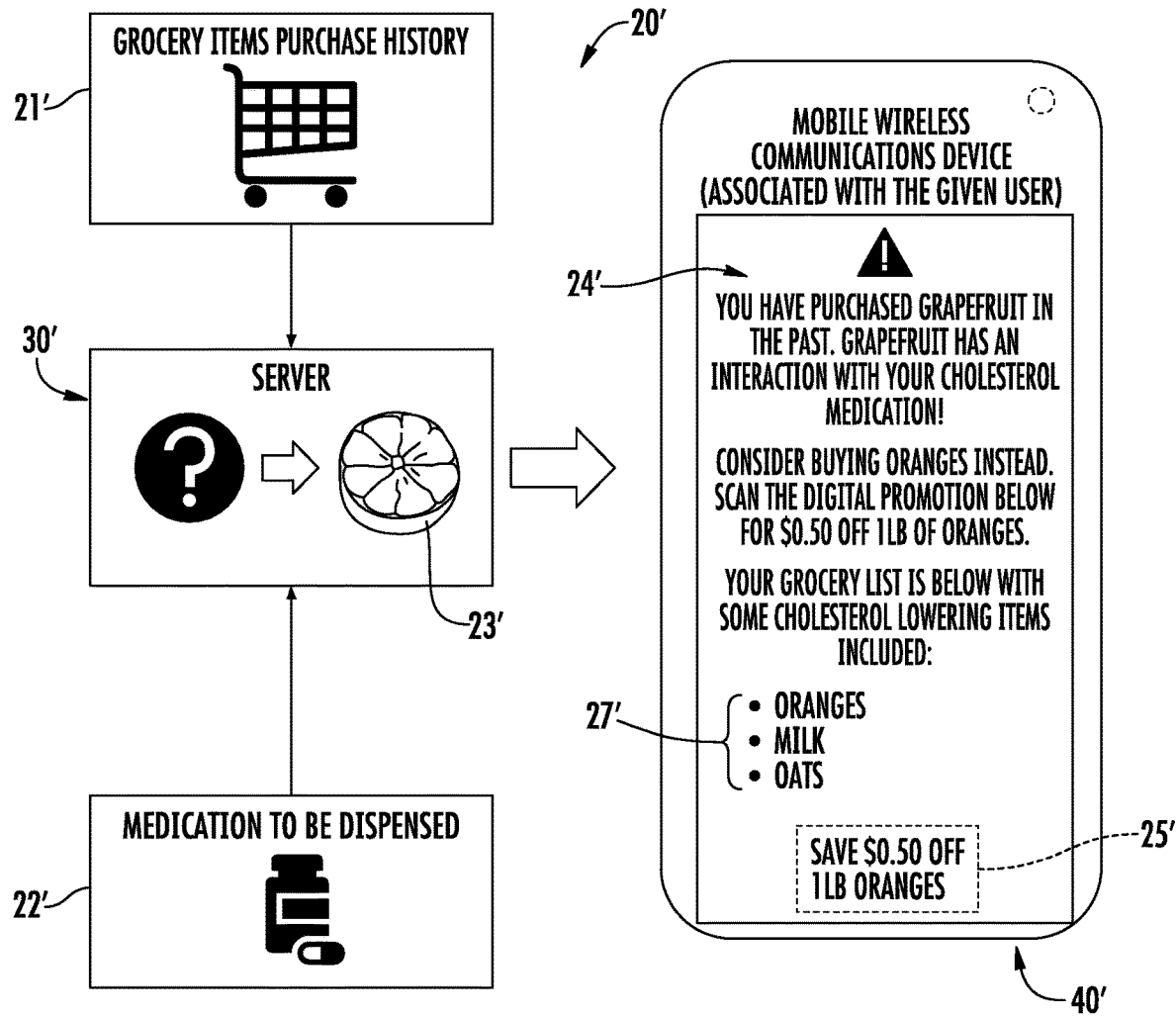
FIG. 4 is a schematic diagram of a system according to another embodiment.

Referring now to FIG. 4, in another embodiment, the remote device 40' may be a mobile wireless communications device associated with the user. Accordingly, the server 30' may generate and communicate the notification 24' of the interaction with the medication along with the digital promotion 25' to the user's mobile wireless communications device 40'. In other words, rather than communicate the notification 24' and digital promotion 25' to a pharmacy POS terminal for printing and providing to the given user, for example, during dispensing of the medication, this information may be communicated directed to the given user. Of course, the server 30' may communicate this information at any time, for example, upon submission of a prescription for the medication, etc.

A method aspect is directed to a method of communicating a digital promotion 25. The method includes using a server 30 to store a grocery items purchase history 21 for a given user, and determine a medication 22 to be dispensed to the given user. The method also includes using the server 30 to compare the medication 22 to the grocery items purchase history 21 and determine a grocery item having an interaction with the medication, and determine a substitute grocery item 23 for the grocery item having the interaction with the medication. The method further includes using the server 30 to generate the digital promotion 25 for the substitute grocery item 23, and communicate the digital promotion to a remote device 40.

A computer readable medium aspect is directed to a non-transitory computer readable medium for communicating a digital promotion 25. The non-transitory computer readable medium includes computer executable instructions that when executed by a processor 30 cause the processor to perform operations. The operations include storing a grocery items purchase history 21 for a given user and determining a medication 22 to be dispensed to the given user. The operations also include comparing the medication 22 to the grocery items purchase history 21 and determine a grocery item having an interaction with the medication and determining a substitute grocery item 23 for the grocery item having the interaction with the medication. The operations further include generating the digital promotion 25 for the substitute grocery item 23, and communicating the digital promotion to a remote device 40.

Many modifications and other embodiments of the invention will come to the mind of one skilled in the art having the benefit of the teachings presented in the foregoing descriptions and the associated drawings. Therefore, it is understood that the invention is not to be limited to the specific embodiments disclosed, and that modifications and embodiments are intended to be included within the scope of the appended claims.

That which is claimed is:

1. A system comprising:
    a mobile wireless communications device associated with a given user having a loyalty account associated therewith, the loyalty account being associated with a name of the given user, the mobile wireless communications device comprising a camera;
    a grocery store point-of-sale (POS) terminal within a grocery store and for processing a purchase of grocery items;
    a pharmacy POS terminal at a pharmacy within the grocery store and for processing a purchase of a medication to be dispensed; and
    a server configured to
        store a grocery items purchase history for the given user based upon the loyalty account,
        determine the medication to be dispensed to the given user by matching the name of the given user to a name associated with the medication, compare the medication to the grocery items purchase history based upon the loyalty account, and determine a grocery item from the grocery items purchase history having an interaction with the medication, determine a level of effect on the given user of the interaction between the grocery item having the interaction and the medication, determine a frequency of purchase of the grocery item having the interaction based upon the grocery items purchase history, generate an interaction score based upon the level of effect on the given user of the interaction and the frequency of purchase of the grocery item having the interaction, a relatively higher interaction score being indicative of causing a higher effect of interaction on the given user, determine whether the interaction score exceeds an interaction threshold score for causing a threshold level of effect of interaction with the given user, and when so determine a substitute grocery item for the grocery item having the interaction with the medication, generate a digital coupon for the substitute grocery item, the digital coupon having a promotional value associated therewith and redeemable at the grocery store POS terminal, adjust the promotional value to increase based upon a higher interaction score, encode the digital coupon as a machine readable digital coupon code, generate a notification of the interaction, communicate the notification and the machine readable digital coupon code to the pharmacy POS terminal so that the notification and the machine readable digital coupon code are printed at the pharmacy POS terminal, and communicate the notification to the mobile wireless communications device;

the mobile wireless communications device configured to display the notification of the interaction, obtain, via the camera, the machine readable digital coupon code from the printed notification, and cooperate with the server to store the digital coupon in a digital wallet for the loyalty account of the given user based upon obtaining the machine readable digital coupon code from the printed notification.

2. The system of claim 1 wherein said server is configured to determine the substitute grocery item based upon a medical condition associated with the medication.

3. The system of claim 1 wherein said pharmacy POS terminal is configured to print a grocery list including the substitute item.

4. The system of claim 1 wherein the machine recognizable code comprises a quick response (QR) code.

5. A system comprising:

a mobile wireless communications device;

a grocery store point-of-sale (POS) terminal;

a pharmacy POS terminal; and a processor and an associated memory configured to store a grocery items purchase history for a given user based upon a loyalty account associated with the given user, the given user being associated with the mobile wireless communications device comprising a camera, and the loyalty account being associated with a name of the given user, determine a medication to be dispensed to the given user by matching the name of the given user to a name associated with the medication, compare the medication to the grocery items purchase history based upon the loyalty account, and determine a grocery item from the grocery items purchase history having an interaction with the medication, determine a level of effect on the given user of the interaction between the grocery item having the interaction and the medication, determine a frequency of purchase of the grocery item having the interaction based upon the grocery items purchase history, generate an interaction score based upon the level of effect on the given user of the interaction and the frequency of purchase of the grocery item having the interaction, a relatively higher interaction score being indicative of causing a higher effect of interaction on the given user, determine whether the interaction score exceeds an interaction threshold score for causing a threshold level of effect of interaction with the given user, and when so determine a substitute grocery item for the grocery item having the interaction with the medication, generate a digital coupon for the substitute grocery item, the digital coupon having a promotional value associated therewith and redeemable at the grocery store POS terminal within a grocery store for processing a purchase of grocery items, adjust the promotional value to increase based upon a higher interaction score, encode the digital coupon as a machine readable digital coupon code, generate a notification of the interaction, communicate the notification and the machine readable digital coupon code to the pharmacy POS terminal at a pharmacy within the grocery store so that the notification and the machine readable digital coupon code are printed at the pharmacy POS terminal, communicate the notification to the mobile wireless communications device so that the mobile wireless communications device displays the notification of the interaction, obtain the machine readable digital coupon code from the printed notification, the printed notification being obtained by the mobile wireless communications device from the printed notification via the camera, and store the digital coupon in a digital wallet for the loyalty account of the given user based upon obtaining the machine readable digital coupon code from the printed notification.

6. The system of claim 5 wherein said processor is configured to determine the substitute grocery item based upon a medical condition associated with the medication.

7. A method of communicating a digital coupon within a system comprising a mobile wireless communications device, a grocery store point-of-sale (POS) terminal, and a pharmacy POS terminal, the method comprising:

using a server to store a grocery items purchase history for a given user based upon a loyalty account associated with the given user, the given user being associated with the mobile wireless communications device comprising a camera, and the loyalty account being associated with a name of the given user, determine a medication to be dispensed to the given user by matching the name of the given user to a name associated with the medication, compare the medication to the grocery items purchase history based upon the loyalty account, and determine a grocery item from the grocery items purchase history having an interaction with the medication, determine a level of effect on the given user of the interaction between the grocery item having the interaction and the medication, determine a frequency of purchase of the grocery item having the interaction based upon the grocery items purchase history, generate an interaction score based upon the level of effect on the given user of the interaction and the frequency of purchase of the grocery item having the interaction, a relatively higher interaction score being indicative of causing a higher effect of interaction on the given user, determine whether the interaction score exceeds an interaction threshold score for causing a threshold level of effect of interaction with the given user, and when so determine a substitute grocery item for the grocery item having the interaction with the medication, generate the digital coupon for the substitute grocery item, the digital coupon having a promotional value associated therewith and redeemable at the grocery store POS terminal within a grocery store for processing a purchase of grocery items, adjust the promotional value to increase based upon a higher interaction score, encode the digital coupon as a machine readable digital coupon code, generate a notification of the interaction, communicate the notification and the machine readable digital coupon code to the pharmacy POS terminal at a pharmacy within the grocery store so that the notification and the machine readable digital coupon code are printed at the pharmacy POS terminal, communicate the notification to the mobile wireless communications device so that the mobile wireless communications device displays the notification of the interaction, obtain the machine readable digital coupon code from the printed notification, the printed notification being obtained by the mobile wireless communications device from the printed notification via the camera, and store the digital coupon in a digital wallet for the loyalty account of the given user based upon obtaining the machine readable digital coupon code from the printed notification.

8. The method of claim 7 wherein using the server comprises using the server to determine the substitute grocery item based upon a medical condition associated with the medication.

9. A non-transitory computer readable medium for communicating a digital promotion within a system comprising a mobile wireless communications device, a grocery store point-of-sale (POS) terminal, and a pharmacy POS terminal, the non-transitory computer readable medium comprising computer executable instructions that when executed by a processor cause the processor to perform operations comprising:

storing a grocery items purchase history for a given user based upon a loyalty account associated with the given user, the given user being associated with the mobile wireless communications device comprising a camera, and the loyalty account being associated with a name of the given user;

determining a medication to be dispensed to the given user by matching the name of the given user to a name associated with the medication;

comparing the medication to the grocery items purchase history based upon the loyalty account, and determine a grocery item from the grocery items purchase history having an interaction with the medication;

determining a level of effect on the given user of the interaction between the grocery item having the interaction and the medication;

determining a frequency of purchase of the grocery item having the interaction based upon the grocery items purchase history;

generating an interaction score based upon the level of effect on the given user of the interaction and the frequency of purchase of the grocery item having the interaction, a relatively higher interaction score being indicative of causing a higher effect of interaction on the given user;

determining whether the interaction score exceeds an interaction threshold score for causing a threshold level of effect of interaction with the given user, and when so determining a substitute grocery item for the grocery item having the interaction with the medication, generating the digital coupon for the substitute grocery item, the digital coupon having a promotional value associated therewith and redeemable at the grocery store POS terminal within a grocery store for processing a purchase of grocery items, adjusting the promotional value to increase based upon a higher interaction score, encoding the digital coupon as a machine readable digital coupon code, generating a notification of the interaction, communicating the notification and the machine readable digital coupon code to the pharmacy POS terminal at a pharmacy within the grocery store so that the notification and the machine readable digital coupon code are printed at the pharmacy POS terminal, communicating the notification to the mobile wireless communications device so that the mobile wireless communications device displays the notification of the interaction, obtain the machine readable digital coupon code from the printed notification, the printed notification being obtained by the mobile wireless communications device from the printed notification via the camera, and store the digital coupon in a digital wallet for the loyalty account of the given user based upon obtaining the machine readable digital coupon code from the printed notification.

10. The non-transitory computer readable medium of claim 9 wherein the instructions comprise determining the substitute grocery item based upon a medical condition associated with the medication.

* * * * *